(12) United States Patent
Manigel et al.

(10) Patent No.: US 9,623,176 B2
(45) Date of Patent: Apr. 18, 2017

(54) PUMP COMPATIBILITY TEST

(71) Applicant: DRÄGER MEDICAL GMBH, Lübeck (DE)

(72) Inventors: Jürgen Manigel, Klingberg (DE); Markus Straähle, Lüdersdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 534 days.

(21) Appl. No.: 14/090,435

(22) Filed: Nov. 26, 2013

(65) Prior Publication Data

US 2014/0163919 A1 Jun. 12, 2014

(30) Foreign Application Priority Data

Nov. 30, 2012 (DE) .................. 10 2012 023 412

(51) Int. Cl.
*A61M 5/168* (2006.01)
*A61M 5/172* (2006.01)

(52) U.S. Cl.
CPC ............ *A61M 5/168* (2013.01); *A61M 5/172* (2013.01); *A61M 5/1723* (2013.01); *A61M 2205/3576* (2013.01); *A61M 2205/50* (2013.01); *A61M 2205/52* (2013.01)

(58) Field of Classification Search
CPC .... A61M 5/168; A61M 5/172; A61M 5/1723; A61M 2205/50; A61M 2205/52; A61M 2205/3576
See application file for complete search history.

(56) References Cited

U.S. PATENT DOCUMENTS

| 7,155,639 B2 | 12/2006 | Gorshenev et al. |
| 7,623,981 B2 | 11/2009 | Achkar et al. |
| 2005/0273681 A1 | 12/2005 | Hopkins |

FOREIGN PATENT DOCUMENTS

WO  2008/025183 A2  3/2008

OTHER PUBLICATIONS

Bressan et al., Automation in Anesthesia: Computer Controlled Propofol Infusion and Data Acquisition, Aug. 20-24, 2008, 30th Annual International IEEE EMBS Conference, Vancouver, British Columbia, Canada, pp. 5543-5547.*
Kim et al., Safety-Assured Development of the GPCA Infusion Pump Software, Oct. 9-14, 2011, EMSOFT' 11, Taipei, Taiwan, pp. 155-164.*

(Continued)

*Primary Examiner* — Toan Le
(74) *Attorney, Agent, or Firm* — McGlew and Tuttle, P.C.

(57) ABSTRACT

A testing device (10), an infusion pump or another medical device function testing method, to an anesthesia apparatus or respirator (AB) and to a computer program product are provided for testing the function of an infusion pump (G). The testing device (10) is preferably implemented on the anesthesia apparatus or respirator (AB) and comprises a memory (MEM), a test module (T) and a controller (C). The test module (T) sends a test command (20) to the infusion pump (FG), which sends a response (30) back to the controller (C) after execution of the command. The control (C) can then compare the response (30) received with a reference response (30') for agreement in order to send a successful function test result.

20 Claims, 2 Drawing Sheets

(56) References Cited

OTHER PUBLICATIONS

L.S Chin, D.J. Worth and C. Greenough, "A Survey of Software Testing Tools for Computational Science", Software Engineering Group, Computational Science & Engineering Department, Rutherford Appleton Laboratory, Harwell Science and Innovation Campus, Didcot, Oxfordshire OX11 0Qx, RAL-TR-2007-010, Jun. 29, 2007.
"Softwaretest", http://web.archive.org/web/20121016122340/http://de.wikipedia.org/wiki/Softwaretest, Jul. 3, 2013.
RTCA—DO-178 B: "Software Considerations in Airborne Systems and Equipment Certification" accessed from the RTCA—organization web site: http://www.rtca.org/, Dec. 1, 1992.

\* cited by examiner

PUMP COMPATIBILITY TEST

CROSS REFERENCE TO RELATED APPLICATIONS

This application claims the benefit of priority under 35 U.S.C. §119 of German Patent Application DE 10 2012 023 412.0 filed Nov. 30, 2012, the entire contents of which are incorporated herein by reference.

FIELD OF THE INVENTION

The present invention pertains to the fields of medical engineering and electronics. The present invention pertains, in particular, to a technical method for the later release of device combinations in a system of medical devices, especially in the areas of intensive care and anesthesia.

BACKGROUND OF THE INVENTION

As a rule, a plurality of different technical devices, which are connected together into a system, interact in modern medical systems. The system may comprise, for example, patient monitors, infusion pumps, anesthesia apparatuses or respirators and/or further medical modules and systems (likewise comprising software systems, such as patient data management systems).

The individual devices and components of the medical system (e.g., patient monitor, infusion pump, anesthesia apparatus and/or respirator, etc.) exchange data via specific communication interfaces. Furthermore, interfaces to external processing systems may be provided, for example, to patient data management systems. It is known that the compatibility of two communication partners is required (is to be ensured). Provisions are made for this that specified test cases are carried out in advance on the respective device to be tested. This has hitherto been carried out manually by a systems engineer, who had to operate the device in question.

However, this procedure has proved to be disadvantageous for various reasons. An enormous amount of maintenance and high costs are associated with it. As soon as a new software update has been installed on one of the devices, it is necessary for regulatory reasons to demonstrate the compatibility in the context of the entire system.

Another difficulty can be seen in the fact that the respective components and devices of different manufacturers are combined into an overall complete (global) medical system. As soon as one of the devices of the overall system has been modified (either by modifying the software, firmware or by other changes), the possibility arises that non-verified device combinations may exist in the overall system. This has to be ruled out with certainty. The previous manual procedure implies the risk that the operator of the system or the client (e.g., the hospital) operates the respective combination of devices without verification and upon their own responsibility. Furthermore, a drawback can be seen in the fact that the respective device manufacturer has no knowledge of the respective device combinations being operated, which may not possibly be verified. The effort needed for testing the entire system rises herewith.

It is known, for example, in the field of mobile wireless devices and client/server systems from U.S. Pat. No. 7,155,639 that a test module can be loaded on the client side even during the operation of a computer system in order to test the functionality of an application interface (application programming interface—API). An additional control channel is installed in this case in addition to the communication channel between server and client in order to make it possible to process and test the data exchange between client and server on the control channel.

SUMMARY OF THE INVENTION

An object of the present invention is therefore to present a technical implementation, with which the testing of different medical devices, especially infusion pumps, which are operated in a system of devices, can be automated, improved and carried out in an error-free manner. Different program versions, which may be installed on the individual devices, shall also be taken into account here, so that the entire system can be tested for compatibility, even after shipping, without changes being necessary on the device to be tested.

This object is accomplished by the by a testing device, a medical device/system (especially an anesthesia apparatus or respirator system), a computer-implemented method and by a computer program product according to the invention.

The present invention will be described below on the basis of the method. Embodiments, alternative solutions, further features and advantages mentioned in this connection may just as well be extrapolated to other solutions according to which the above-mentioned object is accomplished (i.e., to the computer program product and to the testing device and/or device) and vice versa. Accordingly, the features, which are claimed and/or described in connection with the testing device, may also be applied to the method, device or computer program product and vice versa. The respective functional features of the method are implemented by corresponding microprocessor modules or hardware modules, which are designed to assume the respective functionality.

According to one aspect, the present invention pertains to a method for testing the function of an infusion pump, a dispensing pump, a perfusion means or another medical device, which is operated in a medical system of devices. The system of devices may comprise, for example, a patient monitor, an anesthesia apparatus and/or respirator and/or further medical engineering applications. The devices of the system of devices interact via a communication protocol. At least some of the medical devices of the system of devices comprise a memory, in which a program (e.g., firmware) is stored. The program may be installed in various versions. The device can thus be operated with different program versions, so that the system of devices can also be configured differently.

The method comprises the following method steps:

The provision of a set of test commands. The test commands are preferably provided on a testing device and are intended to be executed on the infusion pump or on the medical device to be tested. The test command is designed such that an unambiguous response can be assigned as a reference response in case of correct and error-free function. In other words, the respective test command is designed such that a reference response can be expected to the test command in case of correct operation of the medical device. The assignment between the respective test command and the expected reference response is preferably stored in the testing device.

The testing phase proper can be initiated after conclusion of a preparatory phase by a testing state being activated on the medical device.

After activation of the testing state, at least one test command is sent from the set of test commands provided from the testing device to the infusion pump or to the medical device to be tested via the communication protocol.

The test command sent is then executed on the infusion pump or on the medical device to be tested. After the test command has been executed completely, the infusion pump or medical device generates a response signal or a response message, which is sent back to the testing device via the communication protocol. The response message comprises the response to the test command and may also comprise, moreover, further metadata (e.g., time data, version data, position data, etc.).

The response received can then be extracted (e.g., decoded and separated from other data sets) from the response message and compared with the respective reference response for agreement on the testing device. If the response received agrees with the reference response assigned to the test command, a successful function test result can be sent, which may possibly also be forwarded to further instances of the system of devices and/or to further external instances.

The terms used in connection with this application will be explained in more detail below.

The term "function test" is defined comprehensively and also includes the testing of the respective device to be tested for error-free operation. In addition, testing comprises a version test of the connected components of the system of devices and thus checks the permissibility of different versions of the device. In addition, a compatibility test is comprised as well. An advantageous aspect of the solution according to the present invention can be seen in that the function test also comprises an interface test. The interface between the device, on which the testing device is installed, and connected devices to be tested can thus be checked as well. If, for example, the communication interface is interrupted (e.g., due to a defective or missing network connection), this is detected on the testing device, because no corresponding response signal can be received to the test command sent. To make it possible to image short-term bandwidth fluctuations of the network in this case, provisions are made in a preferred embodiment of the present invention for a time threshold value to be able to be preconfigured here, within which the response must be received to the corresponding test command on the testing device. A corresponding error signal is sent as soon as this threshold value is exceeded.

The medical device is preferably an infusion pump or dispensing pump. However, the provision of other electronic, medical devices, which shall be integrated within the system of devices, is also within the framework of the present invention. These medical devices may be, for example, a patient monitor, an anesthesia apparatus, a respirator, a patient data management device and/or further medical applications, besides the infusion pump.

The testing device is preferably installed on one of the devices of the system of devices, e.g., on an anesthesia apparatus or respirator. However, it may also happen that the testing device is installed on another device or on an external device, which exchanges data with the other devices of the system of devices.

The communication protocol may be a standardized protocol of a local network (LAN—Local Area Network) or of a WAN network (Wide Area Network). It is also possible, moreover, to provide a wireless communication, so that the respective devices interact, for example, via Bluetooth or via other wireless protocols.

A "test command" may be an individual test command, which requests, for example, a data polling from another medical device (e.g., a request command). In addition, it is possible for the test command to comprise, in turn, a plurality of test commands, which shall be executed on the infusion pump or on the medical device to be tested. In a simplified example, a test command could be, for example, as follows: "The biomedical assistant shall set a flow rate of 10 mL/hr. on the infusion pump." A certain reference response can be expected to this test command. The reference response is characterized in this case, for example, in that the data detected will arrive in the correct format, in the correct order and/or in the correct time sequence and are transmitted to the testing device. Furthermore, a checking is performed therewith to determine whether response signals are transmitted back from the medical device to be tested to the testing device at all. It is thus possible to analyze whether the respective partner of the test command (i.e., the receiver of the test command) also behaves "as expected." If the respective test command does not expect a response signal in the proper sense of the word, it is possible to make a setting according to which at least one verification signal is transmitted as a response message to the testing device in case of successful data transmission in order to signal a successful data transmission and execution of the command. A test command is usually a data query, which comprises as a response a defined sequence of detected data. As an alternative, other commands may be provided here, which shall be executed on the device to be tested. These may be commands that are executed fully automatically (the picking up of signals and/or values) or are executed manually by a user directly on the medical device to be tested.

The test command may comprise a simulation command in an advantageous embodiment of the present invention. The simulation command is used not to execute the command on the device to be tested, but to only simulate it and to detect simulated result values, which will then be sent to the controller for checking, as a response signal.

If the drug concentration in the blood is calculated, e.g., by means of pharmacokinetic models based on the dispensing rate of the drug, the time needed to transmit the actual rate of dispensing via the protocol is decisive for the error analysis. In case of usual dispensing rates of up to 1,600 mL/hr., the error would be at most 0.44 mL/sec due to a delay in the transmission protocol caused by the fact that the sampling rate cannot be selected as desired. When changing the dispensing rate from, e.g., 1,600 mL/hr. to zero and with a transmission delay of, e.g., 10 sec, the error in volume would be more than 4 mL, which would not be acceptable any more in many cases. Thus, the dynamic behavior of the transmission protocol affects the error with which the pharmacokinetic models are calculated.

According to a variant of the present invention, a simulation command can be executed on the device to be tested in order to reduce the dispensing rate to a command from the testing device. The new simulated dispensing rate is transmitted back to the testing device via the normal data transmission pathway. The value that the maximum error of calculation can reach can be inferred from the time difference between the command for adjusting the dispensing rate and the execution of the command. A decision on whether the quality or the behavior of the transmission protocol is suitable for the type of application (or on whether it can be operated error-free) can, in turn, be inferred from this on the testing device.

Different configurations can be set in a preparatory phase. In particular, the test commands can be generated during this phase. Furthermore, the reference responses to the respective test command can be defined and assigned to the latter (the assignment is preferably stored in a memory component). Provisions are made in a preferred variant of the present invention for the assignment between test command and reference response to take into account the entire configuration of the system of devices. In particular, the assignment between test command and reference response may consequently be system-specific. It is also possible for the assignment between test command and reference response to be specific of the status of the device (especially version-specific) and/or configuration-specific. "Configuration-specific" means in this connection the configuration of the entire system and it also takes into account the different versions of the device. Different versions of firmware, which are installed on the individual components or devices of the system of devices, are thus taken into account as well. If, for example, the infusion pump is integrated in the system of devices in a first version, it may happen that the test command X generates a reference response, whereas the reference response $Y^2$ is expected if the infusion pump is being operated in another version. The different versions and configurations are taken into account in the function test in this case.

Following execution of the respective test command on the medical device to be tested, the device sends a response message to the testing device. The response message comprises the response. The response may be a signal, a sequence of signals (e.g., a sequence of parameter values or a sequence of acquired measured values, e.g., oxygen saturation, etc.). However, the response may also be only a binary signal, which is implemented, for example, as a flag, and shall signal the case in which the test command was executed properly and the cases in which it was executed with an error. In an advantageous variant of the present invention, the response message also comprises further data, which are sent into one or more packets (packetized) as a response message (e.g., in a coded form and/or with additional metadata) via the communication protocol to the testing device, in addition to the response proper.

It is possible as an alternative that the response is identical to the response message. The response generated on the device to be tested is sent back in this case to the respective test command immediately and unchanged as a response message to the testing device.

The "function test result" may be coded in the binary form in the simplest case and signal essentially two states: Error-free test command execution and erroneous test command execution. Moreover, the function test result may also comprise further metadata, for example, the time at which the test is executed, the duration of execution of the test, display of the respective functions, display of the active devices of the system of devices, etc.

As was already mentioned above, the function testing method is divided primarily into two phases: A configuration phase or preparatory phase, during which different configurations can be set, and a testing phase, during which the testing proper of the device or of the infusion pump is carried out.

According to one aspect, the function test is carried out fully automatically, so that no further interactions are necessary on the part of the user. It is also possible, as an alternative, to carry out the function test semi-automatically, so that, for example, actions must be performed by the user on the infusion pump as a response to the test command. Corresponding signals can now be detected as a response and sent back to the testing device.

Provisions are made in an advantageous variant of the present invention for the function test result to be made automatically available on other instances. This is found to be advantageous especially if a plurality of infusion pumps or medical devices of the same design are integrated in the system of devices. If the function test could lead to a positive test result for one of the devices, this test result can also be made automatically available for the other medical devices of the same design, so that the testing is no longer necessary on the other devices and may advantageously be eliminated, or the other devices that are identical in terms of construction and function are automatically considered to be verified. Release for the other devices of the same design can thus be achieved as well. Furthermore, it is possible to also make device releases available later if medical devices of the same design are connected to the system of devices later on. It is thus no longer necessary to test the newly connected devices if successful function test results could be acquired for this type of design.

According to one aspect of the present invention, the testing device is installed on a device of the system of devices, for example, as an auxiliary electronic module, which can also be installed or implemented on the device later. As an alternative, the testing device may, however, also be installed as a central service on a server, which can be accessed from the medical devices, for example, via a network. It is also possible that the testing device is provided on a separate test module, which is intended for the testing.

According to one aspect of the present invention, the medical devices to be tested are integrated in the system of devices without further changes or adaptations or additional installations. The medical devices to be tested are consequently operated as intended in the particular application. The data or signals detected in the process are passed on as response signals to the testing device. Consequently, no additional installations need to be advantageously performed on the medical device to be tested.

However, it is also possible in an alternative embodiment of the present invention that an additional test routine is implemented on at least one of the medical devices to be tested. The test routine is used as a partner for the testing device, which is installed on a respective other medical device of the system of devices. The testing device sends test commands to the test routine, which may be designed, on the one hand, to execute the test commands received and to send the corresponding response signals back to the testing device and which may be designed, on the other hand, to execute additional test procedures in response to the test command on the medical device to be tested. The result (successful or not successful) may likewise be transmitted to the testing device.

The function test is usually initiated by the testing device. The testing device may be installed on an anesthesia apparatus or respirator or on another medical device (e.g., a workstation, on which a patient data management system is installed, a device on which an expert system for supporting decisions during the operation of the device is installed).

The function test is initiated in the above-described exemplary embodiment by the device on which the testing device is installed (e.g., by a patient monitor or an anesthesia apparatus). However, it may also happen as an alternative that the function test is initiated by the device to be tested. Provisions may be made, for example, for a function test to be initiated automatically if the system of devices recognizes that a new device is integrated into the system of devices. It is also possible that the function test is triggered by a central control means. The triggering of the function test may be performed in an event-controlled and/or time-controlled manner.

To also inform the manufacturer of the respective medical devices of the outcome of the function test, provisions are made in a preferred variant of the present invention for the respective function test result to be also transmitted automatically to other computer-based instances (especially to the device manufacturer) in order to inform the latter of the current status of the combinations being operated and found permissible according to the test.

According to one aspect of the present invention, the test commands are provided on the medical device on which the testing device is installed, whereas the test commands per se are executed on the communication partner, especially the receiver of the test command and consequently on the medical device to be tested. The test proper is carried out by comparing the response received with the respective reference response on the testing device. The function test can thus be executed out as a distributed system, and especially as a client-server system, which is provided partly on the testing device and partly on the medical device to be tested.

Thus, the function test checks the functional cooperation of the medical devices, which are integrated within the system of devices.

According to another aspect of the present invention, the object to be accomplished is accomplished by a testing device that is designed for testing the function of an infusion pump or another medical device within a system of devices. The system of devices optionally also comprises, besides the medical device to be tested (which will hereinafter be called infusion pump but is not limited thereto), a monitor, an anesthesia apparatus or a respirator or other medical devices, which exchange data with one another via a communication protocol. The respective medical devices may be integrated in different versions or configurations (e.g., in different firmware versions) in the system of devices.

The testing device comprises a memory, at least one test module and at least one controller. The memory is used to store a set of test commands and a set of reference responses. Exactly one response is always assigned as a reference response to each test command. The reference response is preferably system-specific and/or configuration-specific. The memory is preferably a nonvolatile memory (e.g., EEPROM). The contents of the memory may also be modified during the operation of the testing device.

The test module is intended to send at least one test command from the set of test commands provided (from the memory) via the communication protocol to the respective infusion pump to be tested for processing. The test module may also have further interfaces to external instances, in order to receive, for example, an initiation signal or a test activity signal (the latter is used to trigger the test).

The controller is designed to receive a response to the test command executed on the device to be tested and to compare the response received with the reference response, which is assigned to the respective test command, for agreement. A successful function test result can be sent in case of agreement between response and reference response.

The test module and the controller are accommodated in a common test and controller module in an alternative embodiment of the testing device. The testing device can thus have a simpler and more cost-effective design.

The testing device is provided on a command transmitter, while the device to be tested is used as a command receiver. The command transmitter and/or command receiver may be designed in the form of medical modules and devices, comprising patient monitors, complex medical systems, such as patient data management systems, anesthesia apparatuses, respirators and individual modules, such as infusion pumps or the like.

As an alternative, the testing device may also be provided on a central server, which exchanges data with a test command repository.

Two operating states are provided, in principle, according to a preferred embodiment:
1. A normal operating state and
2. A testing state. The testing state can be activated or initiated by the test activation signal. The controller is preferably designed in this case to activate the testing device upon receiving the test activation signal. The medical device is usually in the functional operating mode and the controller is deactivated.

A special advantage of the solution according to the present invention can be seen in that the memory can be modified and written to at any time. If, for example, the range of function of a device to be tested is expanded and thus it detects additional data as a response to the respective test command upon a certain test command, the reference response is automatically adapted to the respective test command. The permissible reference responses thus comprise the newly detected data and can be taken into account directly in all future function tests.

In an advantageous variant of the present invention, the testing device is additionally provided with a control unit, which comprises sensors and/or actuators, which are designed to execute the test command on the medical device on which the testing device is installed. The control unit generates a control response to the test command and passes this on to the controller. The controller can thereupon perform an additional comparison. The response received from the medical device being tested is thus compared not only with the reference response for agreement, but additionally also with the control response, which is provided on the controller and which is provided on the control unit. The reliability of the test can thus be increased and it is, furthermore, possible to take into account the current behavior over time.

Another solution to the object of the present invention is based on a medical device, especially a patient monitor or an anesthesia apparatus or respirator, which is provided with a testing device that was described above.

An essential advantage can be seen in the fact that the testing device can also be installed later and can also be installed on the medical device after it has been shipped.

An essential aspect of the present invention can be seen in the fact that the medical device to be tested can be tested without any further changes on the device or in the communication protocol. In particular, it is not necessary to provide an additional control channel between the testing device and the infusion pump to be tested. The function test is carried out via the usual communication protocol. In other words, the interface, which is used to operate the medical device to be tested, and the interface, which is used to test the medical device, are identical. Both are represented by the communication protocol, which is provided anyway. This has the substantial advantage that no additional effort is needed for installation and no additional settings need to be made on the device to be tested.

The above-described embodiments of the method according to the present invention may also be designed as a computer program product with a computer program, wherein the computer is prompted to carry out the above-described method according to the present invention when the computer program is downloaded or run on the computer or on another processor of the computer.

An alternative solution to the object of the present invention also comprises a computer program with computer program code for carrying out all steps of the method being claimed or described above when the computer program is run on the computer. The computer program may also be stored on a machine-readable data storage medium.

An alternative solution to the object of the present invention provides for a storage medium, which is intended for storing the above-described, computer-implemented method and can be read by a computer.

It is within the scope of the present invention that not all steps of the method need necessarily to be carried out on one and the same computer instance, but they may also be carried out on different computer instances. The sequence of the method steps may also be varied if necessary.

Moreover, it is possible that individual sections of the above-described method can be carried out in a saleable unit and the other components in another saleable unit, quasi as a distributed system.

Exemplary embodiments, to which the present invention shall not be considered to be limited, will be discussed along with their features and further advantages in the following detailed description of the figures on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
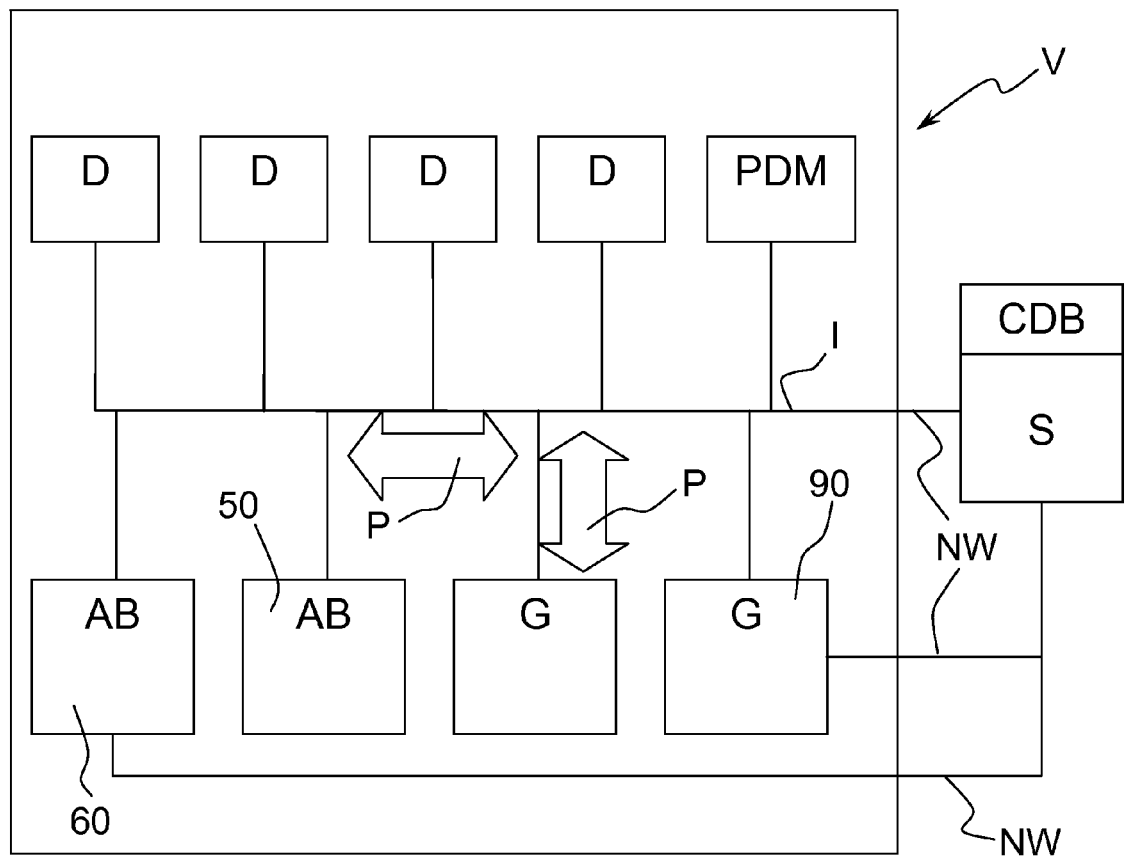
FIG. 1 is a schematic view of a system of medical devices according to the invention.

Referring to the drawings in particular, the present invention will be explained in more detail below on the basis of the Figures.

FIG. 1 schematically shows components of a system of medical devices V, which exchange data with one another via at least one communication protocol P. The exchange of data with one another is via one or more communication channel/communication interface I. In FIG. 1 the interface I, of the system of medical devices V is shown as a network bus, but there may also be individual connections between medical device components and medical device components may also be connected to each other via another component (a series connection). Instead of physical connections (wires/fiber optic), the connections may be via wireless connections between components. Connections via a network NW may also provide a communication channel/interface I for communication with other devices and systems besides the system of medical devices V.

The principal field of application of the present invention is in the fields of intensive care and anesthesia and pertains to a system of medical devices V, which comprises medical devices AB that are associated with the testing and medical devices G that are tested (relative to the medical device AB and/or relative to other or all of the components of the system of medical devices V). The medical devices AB may be, among others, an anesthesia apparatus or a respirator 50 or patient monitor 60. The medical and electronic units to be tested G are also devices in the area of intensive care and anesthesia, for example, an infusion pump 90 may be one of the medical devices G. Further electronic devices (medical devices) AB, for example, a patient monitor 60, are typically also integrated in the system of devices V. In a preferred embodiment, one of the medical devices AB may be, for example, the patient monitor 60 manufactured by Dräger Medical GmbH, which is designed for the stationary monitoring of vital parameters of a patient and can be provided for displaying the parameters with an integrated network adapter and flat screen. Depending on the embodiment, the patient monitor 60 is designed to detect and display a plurality of physiological parameters of the patient, including, for example, ECG data with recognition of arrhythmia, respiration parameters, which are detected, for example, by impedance pneumography, pulse oximetry data, data on the oxygen saturation of the blood (especially of the percentage of oxyhemoglobin relative to the functional hemoglobin), pulse parameters, which are measured, for example, by transmission spectrophotometry, and non-invasively determined blood pressure parameters. The detecting devices or sensors D are connected to the patient monitor 60 (and possibly other medical devices AB) via an appropriate communication channel/interface I.

However, it is also possible, depending on the design, to also integrate further medical devices AB or modules such as detection modules D into the system V. For example, other detection modules D may include an adapter for a device for invasive blood pressure measurement, for measuring the temperature, for gas monitoring, for measuring neurological values, especially EEG parameters, etc., instead of or in addition to the pump (infusion pump or the perfusion means) G. Any of the devices of the system V may be tested according to the invention (may be a medical and electronic units to be tested G). Furthermore, devices that perform a further analysis and processing of the devices detected, especially a patient data management device PDM and further computer-based applications, can be integrated into the system of devices V.

The system of devices V comprises in the preferred embodiment at least one source, at which data are acquired, and a sink-destination (e.g., a device with a microprocessor), which is intended for the processing of the data acquired at the data sources. The source and/or sink are technical devices, which have corresponding interfaces for data exchange and are, as a rule, computer-based. The source and/or sink usually have integrated circuits (e.g., FGPA Field Programmable Gate Array) to implement specific functions.

Figure 2:
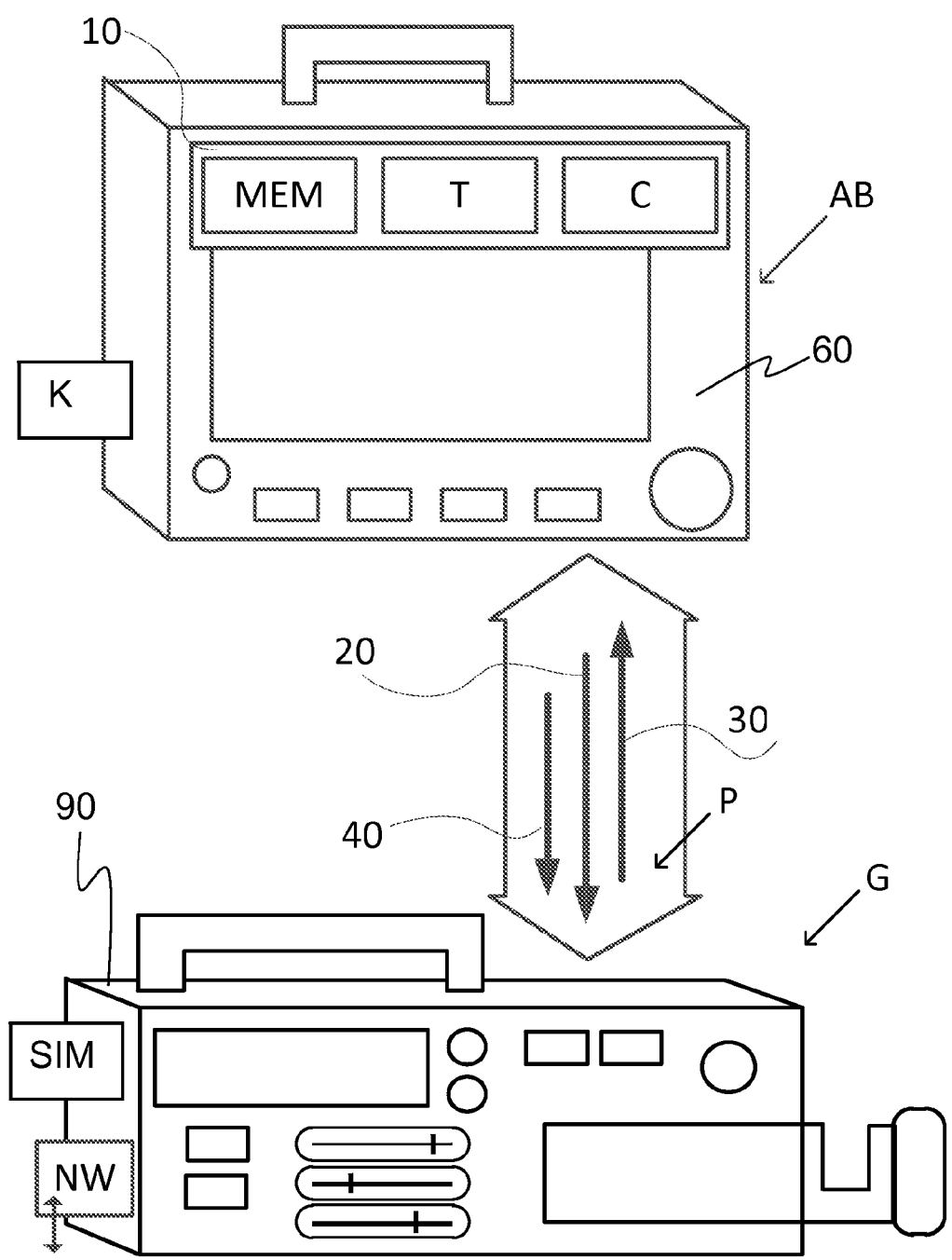
FIG. 2 is a synoptic and schematic view of a medical device with a testing device and with an infusion pump to be tested corresponding to a preferred embodiment of the present invention.

In FIG. 2, the medical device AB is the patient monitor 60 that is coupled with at least one infusion pump 90 as the unit G to be tested (in most applications and in the preferred embodiment of the present invention), which is also shown in FIG. 2. Only a pump G is shown in FIG. 2. However, carrying out simultaneous testing of a plurality of pumps or other devices/units G is expressly also within the framework of the present invention.

The top part of FIG. 2 shows the patient monitor 60 as the medical device AB in this exemplary embodiment. The described method and system and device features can also be used with the anesthesia apparatus or respirator 50 as the medical device AB. The patient monitor AB communicates via the communication protocol P with the infusion pump 90 as the medical device G (shown at the bottom). Furthermore, further medical devices G may be integrated within the system V as well as shown in FIG. 1.

It is seen in practice that the respective electronic or computer-based medical devices (patient monitor 60, pump 90, measuring device D, etc.) are operated with different software/firmware versions or device versions (having different designs), which must be verified and released in a combination. For example, it is thus possible that the pump G can be operated with a first software version of the patient monitor AB and functions, whereas it will not function any more with a second software version of the patient monitor. The context is therefore decisive for an error-free operation of the entire system of devices V. All connected subsystems with their software versions and configurations are to be taken into account. To make matters worse, the individual devices G originate from different manufacturers and the other devices with which the devices G must interact are thus determined only after delivery of the respective device.

The testing device and the testing method being disclosed make it possible that release or checking for an error-free function can be ensured in the system of medical devices V even later, especially after delivery of the respective devices G. This testing can be carried out in a fully automated manner.

The communication protocol P (operating on the communication channel/interface I) is provided for processing the data on the patient monitor AB, which data are generated at the infusion pump G. For example, the name of the drug and the dilution of the drug as well as the volume applied and the current dose rate are transmitted from the infusion pump G via the communication protocol P. The communication protocol P is implemented in the infusion pump G in a manufacturer-specific manner.

The system of medical devices V is provided with or is associated with the testing device 10. As discussed further below, this may be a unit, or it may be integrated into one of the medical devices AB as shown in FIG. 2. The testing device 10 may be connected to the system of medical devices V via the network NW and may comprise software on a server S. The testing device 10 comprises a memory MEM, a test module T and a controller C. The memory stores a set of preconfigured test commands 20. The respective response 30', that is expected to the respective test command 20 is also stored on the memory MEM and are associated with the preconfigured test commands 20.

Additional data packets (data packets in addition to normal operational data packets) are sent, according to the present invention, via exactly the same communication channel/interface I using the same communication protocol P, for testing the device G. As is shown in FIG. 2, the patient monitor AB sends at least one test command 20 to the infusion pump G. The test command may also comprise a plurality of command sequences. However, it may also be a monolithic command block as an alternative. A set of possible test commands 20 is provided for this on the patient monitor AB, and these possible test commands 20 may then be selected in an application-specific manner. However, the test command is not executed directly on the patient monitor AB or on the device on which the testing device 10 is installed, but it is transmitted first via the communication protocol P to the infusion pump G in order to be executed there (on the pump). The consequence of the execution of the command is that result data are acquired on the pump G. This may be with sensors or detection devices D connected directly to pump G or that are a part of pump G. The result data may be measured data (for example, EEG data, ECG data, pulse, temperature or further vital parameters of the patient, data on the depth of anesthesia or pharmacokinetic or pharmacodynamic data, etc.). The measured data may be measured or detected by a device D and fed back to pump G to be incorporated in transmissions form pump G or transmitted otherwise to one or more components of the system V. As an alternative, the result data may also be only a signal from pump G, which signals the erroneous execution of the test command or erroneous execution. Thus, a reference response 30, which is transmitted back to the patient monitor AB via the communication protocol P in order to be processed in the testing device 10 there, is thus generated as a response on the infusion pump G.

The testing device 10 is implemented in a patient monitor 60, the device associated with the testing AB in the exemplary embodiment shown in FIG. 2. However, other exemplary embodiments make provisions for the testing device 10 to be also able to be installed on an anesthesia apparatus or a respirator 50, as the device associated with the testing AB. It is also possible that the testing device 10 is installed on the central server S, which likewise exchanges data with the devices G via a network NW.

The testing device 10 comprises a memory MEM designed to store a set of preconfigured test commands 20. The respective response 30' that is expected to the respective test command 20 has been determined in a configuration phase. This expected response is assigned as a reference response 30' to the respective test command 20. Consequently, the memory contains assignments of test commands 20 and reference responses 30'. This can be schematically described as follows:

First test command $20_1$—First reference response $30'_1$
Second test command $20_2$—Second reference response $30'_2$
...
Nth test command $20_n$—Nth reference response $30'_n$.

A special advantage of the present invention can be seen in the fact that the respective test commands 20, the reference responses 30' and/or the assignments between test command and reference response can be dynamically adapted to the respective application in a configuration phase. The reference response 30', expected during error-free operation, is thus system-specific. "System-specific" means, in this context, that the expected reference response 30' takes into account the devices G integrated within the system of devices V with the respective software versions thereof. Furthermore, the assignment between reference response 30' and test command 20 may also be configuration-specific, which means that the respective configuration of the device G and/or of the entire system of devices V is taken into account. In other words, a different reference response 30' can be expected if the respective device G shall be activated or operated with other functions or is coupled in another system of devices V, which also comprises additional devices, or if the respective device G is operated with another software version.

The test module T is designed as a transmission unit in a preferred embodiment and is used to transmit the selected test command 20 to the infusion pump G via the communication protocol P. The test module T as a transmission unit may be provided at a physically different location from other the memory and other components of the testing device 10.

Controller C is designed as a receiving and processing unit and is designed to receive the response 30 received from the infusion pump G to the respective test command 20. The response is then compared with the reference response 30' assigned to the test command 20 for agreement. A successful function test result can be sent in case of agreement. It can thus be ensured that the infusion pump G behaves in exactly the same way as expected in response to the respective test command 20 and delivers the expected and intended response 30 (which agrees with the intended reference response 30').

A process according to a preferred embodiment will be explained in more detail below with reference to FIG. 2.

The function testing method comprises two phases: A configuration phase and a testing phase, which follows the configuration phase but may also be carried out uncoupled therefrom in time.

Different test commands are generated in the configuration phase for different devices G with different software versions and with the different configurations in the entire system of devices V. Expected reference responses 30' to the respective test commands 20 are likewise generated and associated with the latter. The assignment between the respective test command 20 and the expected reference response 30' is stored in the memory MEM. Further method steps may also be carried out here in more complex embodiments of the present invention. Thus, it is possible, for example, to configure the time interval in which the response must arrive in order to rate an excessively long latent period as an error. If a plurality of devices shall be tested simultaneously, it is also possible to make a configuration concerning the device G from which the response 30 received arrives.

The device to be tested must be changed over from an operating mode into a testing mode at the beginning of the testing phase in order to activate the testing state on the medical device G. Provisions may be made for this for the patient monitor 60 (AB) or the testing device 10 to send an activating signal 40 to the device G. The sending of the activating signal 40 may be triggered in a time-dependent manner and/or in an event-dependent manner (e.g., when additional devices G are integrated in the system of devices V, when new software versions are recognized, when a preceding error is recognized, etc.). The transition from one state to another is especially relevant in medical devices used in intensive care and anesthesia to make it possible to guarantee operation of the device without errors in function with certainty.

In a second step of the testing phase, the test command 20 is selected on the testing device 10 and sent to the infusion pump (medical device) G for execution. This step is carried out on the testing device 10 or on the patient monitor AB.

The test command 20 is executed on the infusion pump G to be tested in a third step of the testing phase. Following execution of the command, the response 30 is detected on the pump and a response message is generated from it. The response message may also contain further data, in addition to response 30, for example, time data, version data, network data, address data (e.g., an IP address or another network protocol address of the device G if a plurality of devices G are tested in parallel and simultaneously and in order to make it possible to unambiguously identify the receipt of the responses 30 of these devices on the testing device 10). However, it is also possible that the response 30 is sent back unchanged as a response message to the testing device 10.

After receiving the response message with the response 30 on the testing device 10, the response 30 received can be compared with the reference response 30', which is assigned to the respective test command 20 in the memory MEM.

A successful test result indication is sent in case of agreement. This may result in the system V or part thereof being cleared for operation and/or may be indicated by a display (such as the display of the patient monitor 60). An error signal can be sent (optically and/or acoustically and/or in other data formats) in the absence of agreement. The error signal may prevent operation of the system V or part thereof and/or may be indicated by the display.

The method can carry out another test run after the comparison or outputting of the function test result. The method can thus be carried out repetitively for further test commands 20 for the same device G. It is also possible that a plurality of devices G are tested sequentially and/or simultaneously.

Different response scenarios for the testing according to the present invention will be described below.

A patient monitor 60 (AB) of a first manufacturer contains, for example, data on the communication protocol P of the infusion pump 90 (G), wherein said infusion pump 90 (G) is manufactured by a second manufacturer. The patient monitor 60 (AB) shall then compute further data from the data. The combination of patient monitor 60 (AB) and infusion pump 90 (G) is verified and approved by the first manufacturer. If a software upgrade is later performed on the infusion pump 90 (G) by the second manufacturer, the combination of patient monitor 60 (AB) and infusion pump 90 (G) is not verified any more. The second manufacture is, in principle, unaware of the concrete application in which his infusion pump 90 (G) is operated, especially of the monitor with which it is operated.

In a first application example, the testing device 10 of the patient monitor AB automatically recognizes a modified software version of pump 90 (G) and makes it possible to automatically verify the pump communication protocol P later. A test routine defined and preconfigurable in the testing device 10 is run for this. A sequence of test commands 20, which are executed either automatically and/or manually by a user based on certain instructions, can be implemented for this on the testing device 10. The user may set, for example, set values on the infusion pump 90 (G). Pump 90 (G) subsequently transmits the set values after execution of the test commands 20 via the unchanged and integrated pump export protocol P to the connected patient monitor 60 (AB). The testing device 10, which is installed on the patient monitor 60 (AB), will then process the values received. As soon as the acceptance criteria are met and a successful function test is confirmed, the compatibility between the patient monitor 60 (AB) and the updated pump version G can be declared.

Figure 3:
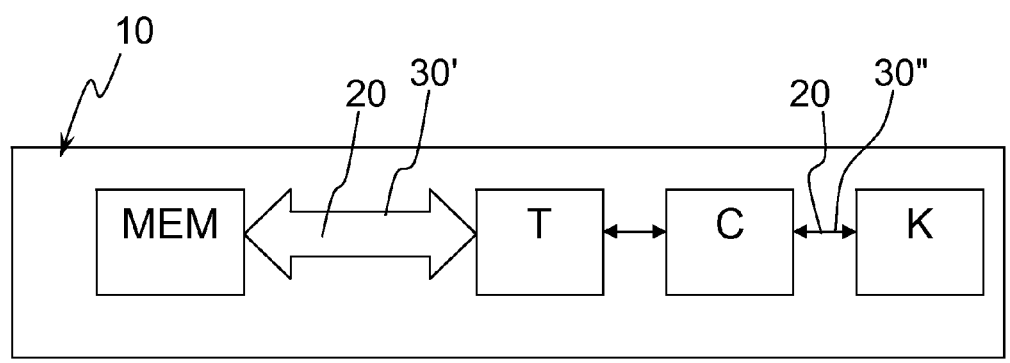
FIG. 3 is a schematic view of features of a testing device.

As shown in FIG. 3, the testing device 10 may be expanded by an additional testing aid in an advantageous variant of the present invention. For example, the testing aid may be a control unit K and especially a flow sensor. The flow sensor is thus used as a reference module for the device G to be tested, in this case the infusion pump G. The flow sensor may likewise be supplied with the test command 20 and it may generate a control response 30" thereupon. The control unit K comprises at least one of sensors and actuators to execute the test command and to generate a control response to the test command. The control unit K passes on the respective generated control response to the controller C. The controller C compares the response received 30" with the control response 30 and with the reference response 30' to check for agreement. It thus becomes possible to compare the response 30 actually received from the infusion pump 90 (G) to be tested with two reference values: With the reference response 30', which is stored in memory M of the testing device 10 anyway, on the one hand, and additionally with the control response 30", which is sent by the testing aid. The flow sensor may additionally also generate further values as a control response 30" in order to make it possible to better analyze the dynamics of the system with the time characteristic thereof. An essential advantage can be seen in the fact that the control unit K is installed temporarily and also can be removed from the device AB immediately after conclusion of the test run. The control unit K is used for an additional checking and hence to increase the reliability of the test.

The device G to be tested may comprise an additional simulation module SIM in another exemplary embodiment. The simulation module comprises an actuator mechanism, control software for the actuator mechanism, interface(s) for data export and for feeding simulation data for exporting the data. The simulation data may be permanently integrated in the infusion pump G. As an alternative, the simulation data may also be set by an external drive. As soon as the patient monitor AB is coupled with the infusion pump G, the testing device 10 starts the simulation on the infusion pump G and either allows the export of a specific data profile or it sets specifically simulated values. Manual operation of the infusion pump G is thus eliminated. This role is played by the simulation software. The function testing can thus be performed fully automatically. The data are exported by the pump G and the exported data are then received at the patient monitor AB and compared with a preconfigured simulation profile for agreement (such as a preconfigured simulation profile saved on memory MEM). A successful function test result is sent in case of agreement.

A successful function test result can be used for further device installations in another example. As soon as the compatibility of a connection infusion pump G is declared by a successful function test result, the patient monitor AB can transmit these data to a central compatibility data bank CDB. The compatibility data bank CDB may also be designed as a repository on a server. The repository transmits the compatibility data either to requesting patient monitors AB upon request or it transmits the compatibility data actively to all patient monitors AB that are currently registered. If there is no compatibility data bank, the rest results may be transmitted manually from a first patient monitor to a second patient monitor. The manufacturer of the patient monitor AB may, of course, also supply the repository with verified compatibility data in advance. In addition, provisions are made for the respective manufacturer of the device (e.g., patient monitor AB) to be able to update, modify or delete the compatibility data at any time.

As was described above, the testing device 10 is usually integrated directly on a patient monitor AB as shown in FIG. 2. However, it is also possible, as an alternative, to accommodate the testing device 10 centrally on a server such as server S, which exchanges data with a patient monitor such as patient monitor 60, a patient data management system, such as patient data management device PDM or other medical devices AB. The respective device AB can download the functional components of the testing device 10, especially the test program, from the server when needed and execute the test program on the device.

The testing device 10 may be implemented in software and/or in hardware. The testing device 10 is preferably integrated or embedded as an embedded system in the patient monitor 60 or in the anesthesia apparatus and/or respirator 50. The testing method is used to store, process and transmit response data, which are exchanged between the device G to be tested and the testing device 10, upon the respective test command. The testing method takes into account especially a modified function process of the respective device G to be tested in such a way that the further components connected to the patient monitor AB and further versions and configurations of the respective programs are tested for the operation of the device G. Individual method steps or even the entire method may be part of a microprocessor solution, which is hard-wired on the testing device 10. All sections or selected sections of the method are coded in the binary form and are in a digital form. All or some sections of the method may be provided as source code, as compiled code (machine code) or as interpreted code (e.g., in different interpreter languages, such as Ruby, PHP, etc.) or may be interpreted by an interpreter (e.g., Jit Compiler).

The patient monitor 60 or the anesthesia apparatus or respirator 50 may comprise, for example, a plurality of processors with individual firmware.

As described above, the testing device 10 comprises the memory MEM, which is directly integrated in the testing device 10 in the preferred embodiment. As an alternative, the memory MEM may also be formed by a memory module, a memory card or a mobile data storage medium (e.g., in the form of a USB stick) in order to increase the flexibility of the assignment between test command 20 and reference response 30'.

In a preferred embodiment, the testing device 10 is activated, in principle, each time before a device G is put into operation and after detection of a change on the system of devices V.

It should finally be mentioned that the description of the present invention and the exemplary embodiments shall be understood as being, in principle, not limiting with respect to a certain physical embodiment of the present invention. It is especially obvious to a person skilled in the art that the present invention can be embodied partly or fully in software and/or hardware and/or distributed among a plurality of physical products, also including especially computer program products.

While specific embodiments of the invention have been shown and described in detail to illustrate the application of the principles of the invention, it will be understood that the invention may be embodied otherwise without departing from such principles.

LIST OF REFERENCE NUMBERS

10 Testing device
G Infusion pump or medical device to be tested
V System of devices
AB Patient monitor or anesthesia apparatus or respirator
P Communication protocol
MEM Memory
T Test module
C Controller
K Control unit
20 Test command
30 Response
30' Reference response
30" Control response
40 Test activation signal
NW Network

What is claimed is:

1. A testing device for testing the function of an infusion pump or another medical device within a system of devices comprising an anesthesia apparatus or respirator, wherein the devices of the system of devices exchange data with one another via a communication protocol and wherein there are different configurations of the system of devices, the testing device comprising:

a memory with stored sets of test commands and with at least one stored reference response assigned to each test command, wherein each of the sets of test commands is configuration specific and the at least one stored reference response is configuration-specific, corresponding to a configuration of system devices of the test command to which the reference response is assigned;

at least one test module activated with a test activation signal to change the infusion pump or the another medical device to a testing state for receiving test commands and generating one or more responses and sending at least one test command from one of the sets of test commands, stored in memory, to the infusion pump or to the another medical device for processing and/or executing the test command with the infusion pump or to the another medical device in the test state, via the communication protocol; and at least one controller receiving a response to the test command, via the communication protocol, that includes data related to execution of the test command by the infusion pump or the another medical device providing an indication that the test command has been executed by the infusion pump or to the another medical device, comparing the response with the at least one stored reference response, assigned to the respective test command, for agreement between the response and the at least one stored reference response related to data arriving in a correct format, in a correct order and in a correct time sequence, and sending a successful function test result indication in case of agreement.

2. A testing device in accordance with claim 1, wherein in the testing device is provided on the anesthesia apparatus or respirator.

3. A testing device in accordance with claim 1, wherein the controller is configured to activate the testing device upon receiving a test activation signal.

4. A testing device in accordance with claim 1, wherein the test command, as a part of a configuration set of test commands, comprises a configuration specific, simulation command.

5. A testing device in accordance with claim 1, wherein the memory is a writeable memory that can be modified at any time by writing other test commands and/or reference responses to the memory.

6. A testing device in accordance with claim 1, further comprising a control unit comprising at least one of sensors and actuators to execute the test command and to generate a control response to the test command, and wherein:
the control unit passes on the respective generated control response to the controller; and
the controller compares the response received with the control response and with the reference response for agreement.

7. A testing device in accordance with claim 1, wherein in the testing device is provided on a patient monitor.

8. A system of medical devices, the system comprising:
a plurality of medical devices comprising one or more devices are connected to and disconnected from or added to the system of medical devices and including at least one device to be tested with respect to operability of at least one other device associated with the testing, wherein the plurality of medical devices are provided as one of a plurality of different configurations of the system of medical devices;
a communication interface connecting the device associated with the testing with the device to be tested;
a communication protocol established between the device associated with the testing and the device to be tested for data exchange with one another via the communication protocol and wherein there are different configurations of the system of devices;
a testing device comprising:
a memory with stored sets of test commands and with at least one stored reference response assigned to each test command, wherein each of the sets of test commands is configuration specific and the at least one stored reference response is configuration-specific, corresponding to a configuration of the system of medical devices of the test command to which the reference response is assigned;
at least one test module activated with a test activation signal to change the device to be tested to a testing state for receiving test commands and generating one or more responses and sending at least one test command from one of the sets of test commands, stored in memory, to the device to be tested for processing and/or executing the test command with the device to be tested in the test state, via the communication protocol; and
at least one controller receiving a response to the test command, via the communication protocol, that includes data related to execution of the test command by the device to be tested providing an indication that the test command has been executed by the device to be tested, comparing the response with the at least one stored reference response, assigned to the respective test command, for agreement between the response and the at least one stored reference response related to data arriving in a correct format, in a correct order and in a correct time sequence, wherein the plurality of medical devices includes an anesthesia apparatus or respirator and the testing device is connected to or provided in or on the anesthesia apparatus or respirator to form at least a part of one of the plurality of different configurations of the system of medical devices.

9. A system in accordance with claim 8, wherein:
the device to be tested is an infusion pump.

10. A system in accordance with claim 9, wherein the controller is configured to activate the testing device upon receiving a test activation signal.

11. A system in accordance with claim 8, wherein the test command comprises a simulation command.

12. A system in accordance with claim 8, wherein the memory is a writeable memory that can be modified at any time by writing other test commands and/or reference responses to the memory.

13. A system in accordance with claim 8, further comprising a control unit comprising at least one of sensors and actuators to execute the test command and to generate a control response to the test command, and wherein:
the control unit passes on the respective generated control response to the controller; and
the controller compares the response received with the control response and with the reference response for agreement.

14. A system in accordance with claim 8, wherein in the testing device is provided connected to, on or as a part of a patient monitor.

15. A system in accordance with claim 8, wherein:
the plurality of medical devices comprise a plurality of medical device modules including an anesthesia apparatus or respirator a modifiable testing device; and
the testing device comprises a modifiable testing device.

16. A system in accordance with claim 8, wherein:
the device to be tested and the device associated with the testing exchange data packets in during normal operation; and
the device to be tested sends the at least one test response as a packetized message via the communication protocol and the testing device sends test commands as a packetized message via the communication protocol.

17. A system in accordance with claim 8, wherein:
the system operates a testing method comprising a configuration phase and a testing phase, which follows the configuration phase but may also be carried out uncoupled therefrom in time.

18. A system in accordance with claim 8, wherein the testing device comprises a computer program product, wherein the computer program product comprises a computer program, which is stored on a data storage medium or in a memory of a computer forming at least a part of the memory with a stored set of test commands or which can be downloaded via a network connection and which comprises computer-readable commands, which are intended for executing method steps when the commands are being executed on the computer.

19. A testing method for testing the function of an infusion pump or of another medical device within a system of devices comprising at least an anesthesia apparatus or respirator, wherein the devices of the system of devices exchange data with each other via a communication protocol and wherein there are different configurations of the system of devices comprising one or more devices connected to and disconnected from or added to the system, with the following method steps:
providing sets of test commands, which are intended to be executed on the infusion pump or on the other medical device, wherein each of the sets of test commands is configuration specific and at least one reference response is assigned to each test command and wherein the reference response is configuration-specific, corresponding to a configuration of the system of devices of the test command to which the reference response is assigned;
activating a testing state on the infusion pump or on the other medical device;
sending of at least one test command, of the set of test commands, via the communication protocol, to the infusion pump or to the other medical device;
executing the test command on the infusion pump or on the other medical device with the infusion pump or to the another medical device in the test state and sending of at least one response message via the communication protocol that includes data related to execution of the test command by the infusion pump or the another medical device providing an indication that the test command has been executed by the infusion pump or the another medical device;
receiving the response and extracting a response from the response message;
comparing the response received with the respective reference response, which is assigned to the test command, for agreement between the response and the at least one stored reference response related to data arriving in a correct format, in a correct order and in a correct time sequence and, in case of agreement, sending of a successful function test result indication.

20. The testing method according to claim 19, further comprising:
providing a computer program product, wherein the computer program product comprises a computer program, which is stored on a data storage medium or in a memory of a computer or which can be downloaded via a network connection and which comprises computer-readable commands, which are intended for executing the method steps when the commands are being executed on the computer.

* * * * *